US006812340B2

(12) United States Patent
Gendron et al.

(10) Patent No.: US 6,812,340 B2
(45) Date of Patent: Nov. 2, 2004

(54) INHIBITION OF BONE TUMOR FORMATION USING ANTISENSE CDNA THERAPY

(75) Inventors: Robert L. Gendron, Cincinnati, OH (US); Helene Paradis, Cincinnati, OH (US)

(73) Assignee: Children's Hospital Research Foundation, Cincinnati, OH (US)

( * ) Notice: Subject to any disclaimer, the term of this patent is extended or adjusted under 35 U.S.C. 154(b) by 0 days.

(21) Appl. No.: 09/836,410

(22) Filed: Apr. 17, 2001

(65) Prior Publication Data

US 2002/0064783 A1 May 30, 2002

Related U.S. Application Data

(60) Provisional application No. 60/197,977, filed on Apr. 17, 2000.

(51) Int. Cl.$^7$ .......................... C07H 21/02; C07H 21/04

(52) U.S. Cl. .................. 536/24.5; 536/24.3; 536/24.31; 536/24.33

(58) Field of Search .......................... 435/6, 91.1, 91.3, 435/375; 536/23.1, 24.5, 24.3, 24.33, 24.31; 514/44

(56) References Cited

PUBLICATIONS

S Agrawal, TIB Tech, "Antisense oligonucleotides:towards clinical trials," Oct. 1996, vol. 14, pp. 376–387.*
WF Anderson, Nature, "Human gene therapy," Apr. 1998, vol. 392, pp. 25–30.*
IM Verma et al., Nature, "Gene therapy–promises, problems and prospects," Sep. 1997, vol. 389, pp. 239–242.*
DW Green et al., American College of Surgeons,"Antisense Oligonucleotides:An Evolving Technology for the Modulation of Gene Expression in Human Disease,"Jul. 2000, vol. 191, No. 1, pp. 93–105.*
K–Y Jen et al., Stem Cells, "Supression of Gene Expression by Targeted Disruption of Messenger RNA: Available Options and Current Strategies," 2000, 18:307–319.*
AD Branch, TIBS, "A good antisense molecule is hard to find," Feb. 1998, pp. 45–50.*
Mullen, J. R., Kayne, P. S., Moerschell, R. P., Tsunasawa, S., Gribskov, M., Colavito Shepanski, M., Grunstein, M., Sherman, F., and Sternglanz, R. Identification and characterization of genes and mutants for an N–terminal acetyltransferase from yeast. EMBO J., 8: 2067–2075, 1989.
Ouchida, M., Ohno, T., Fujimura, Y., Rao, V.N., and Reddy, E.S. Loss of tumorigenicity of Ewing's sarcoma cells expressing antisense RNA to EWS–fusion transcripts. Oncogene, 11: 1049–1054, 1995.
Kovar, H., Aryee, D. N., Jug, G., Henockl, C., Schemper, M., Delattre, O., Thomas G., and Gadner, H. EWS/FLI–1 antagonists induce growth inhibition of Ewing tumor cells in vitro. Cell Growth Differ., 7: 429–437, 1996.
Gendron, R. L., Tsai, F. Y., Paradis, H., Arceci, R. J. Induction of embryonic vasculogenesis by bFGF and LIF in vitro and in vivo. Dev. Biol., 177: 332–346, 1996.

(List continued on next page.)

Primary Examiner—Karen A. Lacourciere
(74) Attorney, Agent, or Firm—Frost Brown Todd LLC

(57) ABSTRACT

As described herein, the present invention comprises a method for using tubedown-1 (tbdn-1) antisense reagents as gene therapy agents for the treatment of bone tumors and Ewing's sarcoma family of tumors. Antisense-based reagents, such as tbdn-1 antisense construct or biologically stabilized oligonucleotides, or any compound which would elicit the downregulation of tbdn-1 level or activity and the same biological effects as tbdn-1 antisense construct on bone tumor growth in vivo provide valuable alternative or supplemental therapies for bone cancer.

13 Claims, 6 Drawing Sheets

PUBLICATIONS

Toretsky, J.A., Connell, Y., Neckers, L., Bhat, N.K. Inhibition of EWS–FLI–1 fusion protein with antisense oligodeoxynucleotides. J. Neurooncol., 31: 9–16, 1997.

Tanaka, K., Iwakuma, T., Harimaya, K., Sato, H., and Iwamoto, Y. EWS–Fli1 antisense oligodeoxynucleotide inhibits proliferation of human Ewing's sarcoma and primitive neuroectodermal tumor cells. J. Clin. Invest., 99: 239–247, 1997.

May, W. A., Arvand, A., Thompson, A. D., Braun, B. S., Wright, M., and Denny, C. T. EWS/FLI1–induced manic fringe renders NIH 3T3 cells tumorigenic. Nat. Genet., 17: 495–497, 1997.

Good, W. V., Paradis, H., Adams, L.C. and Gendron, R. L. Ocular spatial distribution of tubedown–1 (tbdn–1), a novel acetyltransferase regulated in endothelial cell differentiation. The Association for Research in Vision and Opthalmology (ARVO) Annual Meeting May 9–14, 1998, Fort Lauderdale, FL.

Invited participant in *Electronic Workshop on Genetic Manipulation in Animals: Advanced Transgenesis and Cloning*. National Institute of Standards and Technology, U.S. Department of Commerce, Advanced Technology Program Website: http://www.atp.nist.gov/atc/atc–6.htm. Sep., 1998. *Prospects and hurdles in optimizing the vascular support of engineered tissues.*

Fizazi, K., Dohollou, N., Blay, J. Y., Guerin, S., Le Cesne, A., Andre, F., Pouillart, P., Tursz, T., and Nguyen, B. B. Ewing's family of tumors in adults: multivariate analysis of survival and long–term results of multimodality therapy in 182 patients. J. Clin. Oncol., 16: 3736–3743, 1998.

Liebermann, D. A., and Hoffman, B. MyD genes in negative growth control. Oncogene, 17: 3319–3329, 1998.

Gewitz, A. M., Sokol, D. L., and Ratajczak, M. Z. Nucleic acid therapeutics: state of the art and future prospects. Blood., 92: 712–736, 1998.

Gendron, R. L., Adams, L.C. and Paradis, H. Tubedown–1, a novel acetyltransferase associated with vascular remodeling. Experimental Biology '99. Washington, DC, Apr., 1999.

Palumbo, J. S., and Zwerdling, T. Soft tissue sarcomas of infancy. Semin. Perinatol., 23: 299–309, 1999.

Arndt, C. A., and Crist, W. M. Common musculoskeletal tumors of childhood and adolescence. N. Engl. J. Med., 341: 342–352, 1999.

Amann, G., Zoubek, A., Salzer–Kuntschik, M., Windhager, R., and Kovar, H. Relation of neurological marker expression and EWS gene fusion types in MIC2/CD99–positive tumors of the Ewing family. Hum. Pathol., 30: 1058–1064, 1999.

Thompson, A. D., Teitell, M. A., Arvand, A., and Denny, C. T. Divergent Ewing's sarcoma EWS/ETS fusions confer a common tumorigenic phenotype on NIH3T3 cells. Oncogene, 18: 5506–5513, 1999.

Hahm, K. B., Cho, K., Lee, C., Im, Y. H., Chang, J., Choi, S. G., Sorensen, P. H., Thiele, C. J., and Kim, S. J. Repression of the gene encoding the TGF–beta type II receptor is a major target of the EWS–FLI1 oncoprotein. Nat. Genet., 23: 222–227, 1999.

Lin, P. P., Brody, R. I., Hamelin, A. C., Bradner, J. E., Healey, J. H., and Ladanyi, M. Differential transactivation by alternative EWS–FLI1 fusion proteins correlates with clinical heterogeneity in Ewing's sarcoma. Cancer Res., 59: 1428–1432, 1999.

Polevoda, B., Norbeck, J., Takakura, H., Blomberg, A., and Sherman, F. Identification and specificities of N–terminal acetyltransferases from Saccharomyces cerevisiae. EMBO J., 18: 6155–6168, 1999.

Coffman, F. D., and Studzinski, G. P. Differentiation–related mechanisms which suppress DNA replication. Exp. Cell. Res., 248: 58–73, 1999.

Im, S. A., Gomez–Manzano, C., Fueyo, J., Liu, T. J., Ke, L. D., Kim J. S., Lee, H. Y., Stech, P. A., Kyritsis, A. P., and Yung, W. K. Antiangiogenesis treatment for gliomas: transfer of antisense–vascular endothelial growth factor inhibits tumor growth in vivo. Cancer Res., 59: 895–900, 1999.

West, D. C. Ewing sarcoma family of tumors. Curr, Opin, Oncol., 12: 323–329, 2000.

de Alava, E, and Gerald, W. L. Molecular biology of the Ewing's sarcoma/primitive neuroectodermal tumor family. J. Clin. Oncol., 18: 204–213, 2000.

Im, Y. H., Kim, H. T., Lee, C., Poulin, D., Welford, S., Sorensen, P. H., Denny, C. T., and Kim S. J. EWS–FLI1, EWS–ERG, and EWS–ETV1 oncoproteins of Ewing tumor family all suppress transcription of transforming growth factor beta type II receptor gene. Cancer Res., 60: 1536–1540, 2000.

Gendron, R. L., Adams, L. C., and Paradis, H. Tubedown–1, a novel acetyltransferase associated with blood vessel development. Dev. Dyn., 218: 300–315, 2000.

Bromberg, J., Darnell, J. E. Jr. The role of STATs in transcriptional control and their impact on cellular function. Oncogene, 19: 2468–2673, 2000.

Yuen, A. R., and Sikic B. I. Clinical studies of antisense therapy in cancer. Front. Biosci., 1: D588–593, 2000.

Gewirtz, A.M. Oligonucleotide therapeutics: a step forward. J. Ciln. Oncol., 18: 1809–1811, 2000.

* cited by examiner

INHIBITION OF BONE TUMOR FORMATION USING ANTISENSE CDNA THERAPY

This application is based on and claims priority from U.S. Provisional Patent Application Ser. No. 60/197,977, Robert L. Gendron, filed Apr. 17, 2000.

FEDERAL SUPPORT STATEMENT

This work was supported in part by NIH Grant No. U10 CA13539.

FIELD OF INVENTION

The present invention relates to the use of antisense cDNA targeting for the inhibition and/or prevention of tumor growth. More specifically, this invention relates to the use of antisense nucleic acid derived from the antisense cDNA sequence of tubedown-1 for the inhibition and/or prevention of bone tumors, especially osteosarcoma and Ewings Sarcoma family of tumors.

BACKGROUND

Cancer is generally treated with cytoreductive therapies that involve administration of ionizing radiation or chemical toxins that kill rapidly dividing cells. Unfortunately, these therapies are highly toxic to non-cancer cells and cause severe side effects, such as bone marrow suppression, hair loss and gastrointestinal disturbances.

Osteosarcoma, a bone cancer occurring primarily in teen-agers and young adults, affects approximately 2100 individuals yearly in the United States (1). This malignancy accounts for as many as 5% of all childhood malignancies and 60% of all malignant childhood bone tumors (2). Despite radical surgical resection of the primary tumor and aggressive adjuvant chemotherapy, the overall 2-year metastasis-free survival rate approaches only 66%. More than 30% of patients with this disease develop lung metastasis within the first year (3–4). The survival rate among those affected with osteosarcoma has not changed significantly over the past 10 years, despite changes in adjuvant chemotherapy (5).

Ewing's Sarcoma is the second most frequent type of bone tumor and Ewing's Sarcoma most often strikes during the second decade of life. Tumors can metastasize to lungs, other bones and to the bone marrow (6–8). Approximately 25% of Ewing's tumor patients present detectable metastatic disease at diagnosis, but it is probable that most patients have micrometastases (9–10). Approximately 40 percent of Ewing's sarcoma patients do not survive. Extraosseous Ewing's sarcoma variants including the peripheral primitive neuroectodermal tumor (PNET) and the Askin tumor (a thoracic form of Ewing's sarcoma) are more rare (7–8).

Chemotherapy using cytotoxic drugs (vincristine, actinomycin-D, cyclophosphamide, etoposide), followed by surgery or radiotherapy is the current treatment regimen for Ewing's sarcomas (6, 10). There is a 50–70% survival rate (5 years) in cases of localized disease. However, when metastatic disease is observed, there is a 19–30% survival rate (5 years) (10). Moreover, the risk of developing secondary malignancies is approximately 6.7% at 10 years and 43% at 20 years, and relapse 5 years after treatment occurs in approximately 9–16% of cases (7, 9). The intensive radiation and chemotherapy treatments for both osteosarcoma and Ewing's sarcoma tumors are associated with a high degree of toxicity. Thus, new treatments are needed for these types of pediatric bone tumors.

Although the genetic alterations involved in Ewing's sarcoma have been identified, understanding how these pathologically modified genetic pathways lead to and support growth of Ewing's tumors have not been completely realized. The isolation, characterization and practical manipulation of additional regulatory molecules which could play a common role in the growth control of Ewing's sarcoma cells may lead to new and improved therapies for the Ewing's family of tumors. Such new therapy would be aimed at altering the signaling pathways which regulate growth of Ewing's tumor cells and could offer alternatives or supplements to the currently available treatments.

Furthermore, even less is known about the genetics or growth control of osteosarcomas. The isolation, characterization and practical manipulation of master regulatory molecules which could play a common role in the growth control of bone tumor cells may lead to new and more effective therapies for bone cancer. New treatments aimed at altering the signaling pathways which regulate growth of bone tumor cells offers alternatives or supplements to the exclusive use of radiotherapy, cytotoxic chemotherapeutic drugs and surgery.

The inventors have cloned a new gene named tubedown-1 (tbdn-1) which encodes a novel protein associated with an acetyltransferase activity (11). This tubedown-1 protein is highly expressed in primitive bone tumors of mesenchymal and neuroectodermal origin such as osteosarcoma and Ewing's sarcoma. The in vivo expression pattern of tbdn-1 suggests it may play a role in regulating endothelial, hemato-poietic and bone development (FIG. 1) (11). In early myeloid blood cells, blood vessel endothelium and bone, tbdn-1 is expressed at high levels early on and becomes downregulated as these cells mature (11). Tbdn-1 expression distribution during embryogenesis is similar to the expression distribution of FLI-1 (12). In adults, tbdn-1 is restricted to ocular and ovarian blood vessels, bone marrow and atrial endocardium.

Tbdn-1 is also expressed highly in Ewing's sarcoma cells, suggesting that it may play a regulatory role in this type of tumor. This finding implies that tbdn-1 may play a regulatory role in these types of bone cancer and perhaps bone cancer in general. Therefore, one approach to the treatment of these sarcomas would be a gene therapy approach aimed to block expression of tbdn-1 in these bone tumors by inducing expression of an antisense tbdn-1 cDNA fragment (AStbdn-1) which inhibits tumor growth.

SUMMARY OF THE INVENTION

As described herein, the present invention comprises a method to use tbdn-1 antisense reagents as gene therapy agents for the treatment of bone tumors and Ewing's sarcoma family of tumors. Antisense-based reagents, such as tbdn-1 antisense construct or biologically stabilized oligonucleotides, or any compound which would elicit the downregulation of tbdn-1 level or activity and the same biological effects as tbdn-1 antisense construct on bone tumor growth in vivo provide valuable alternative or supplemental therapies for bone cancer.

The antisense cDNA molecules utilized in the present invention generate antisense mRNA of at least 70% complementarity to mRNA produced by a native tubedown-1 gene. Preferred antisense oligonucleotide molecules are selected from the group consisting of SEQ ID NO. 3 and SEQ ID NO. 4. These above-cited antisense oligonucleotides derived from the cDNA sequence of SEQ ID NO. 2, may also be formulated as compositions comprising a safe and effective amount of an antisense oligonucleotide molecule and a pharmaceutically acceptable carrier.

A gene therapy approach for treatment of mammals afflicted with bone tumors, such as Ewing's Sarcoma and osteosarcoma or expressing a tubedown-1 protein is provided. For this method of treatment, a biologically active antisense cDNA is generated from the cDNA of SEQ ID NO. 2 and administered to cells of an individual producing excess of a tubedown-1 gene.

This method further comprises in vivo administration into host cells a replicable vector comprising and expressing the desired antisense cDNA, which in turn produces the antisense mRNA. The vector is then taken up by the cells to produce the antisense mRNA. This antisense mRNA binds to native mRNA produced by the tubedown-1 gene, thereby blocking expression of the gene. The antisense cDNA generates antisense mRNA of at least 70% complementarity to mRNA produced by a native tubedown-1 gene and which can hybridize with the native mRNA under low and high stringency conditions. The preferred antisense cDNA's for use in this gene therapy treatment are selected from the group consisting of SEQ ID NO. 3 and SEQ ID NO. 4 and mixtures thereof.

In an alternative treatment for bone tumors, and Ewings Sarcoma family of tumors and osteosarcoma in particular, single-stranded antisense oligonucleotides derived from the antisense cDNA sequence of SEQ ID NO. 3 or 4 can be generated ex vivo. These antisense oligonucleotides are at least 15 nucleobases in length and preferably at least 25 nucleobases in length. Thus, when introduced into the cell, these antisense oligonucleotides cause inhibition of expression of tbdn-1 by hybridizing with native mRNA and genomic sequences of a tbdn-1 gene. Other biological or chemical factors to inhibit the expression of said tbdn-1 protein are also within the scope of this invention.

DETAILED DESCRIPTION OF THE INVENTION

Definitions

Figure 1:
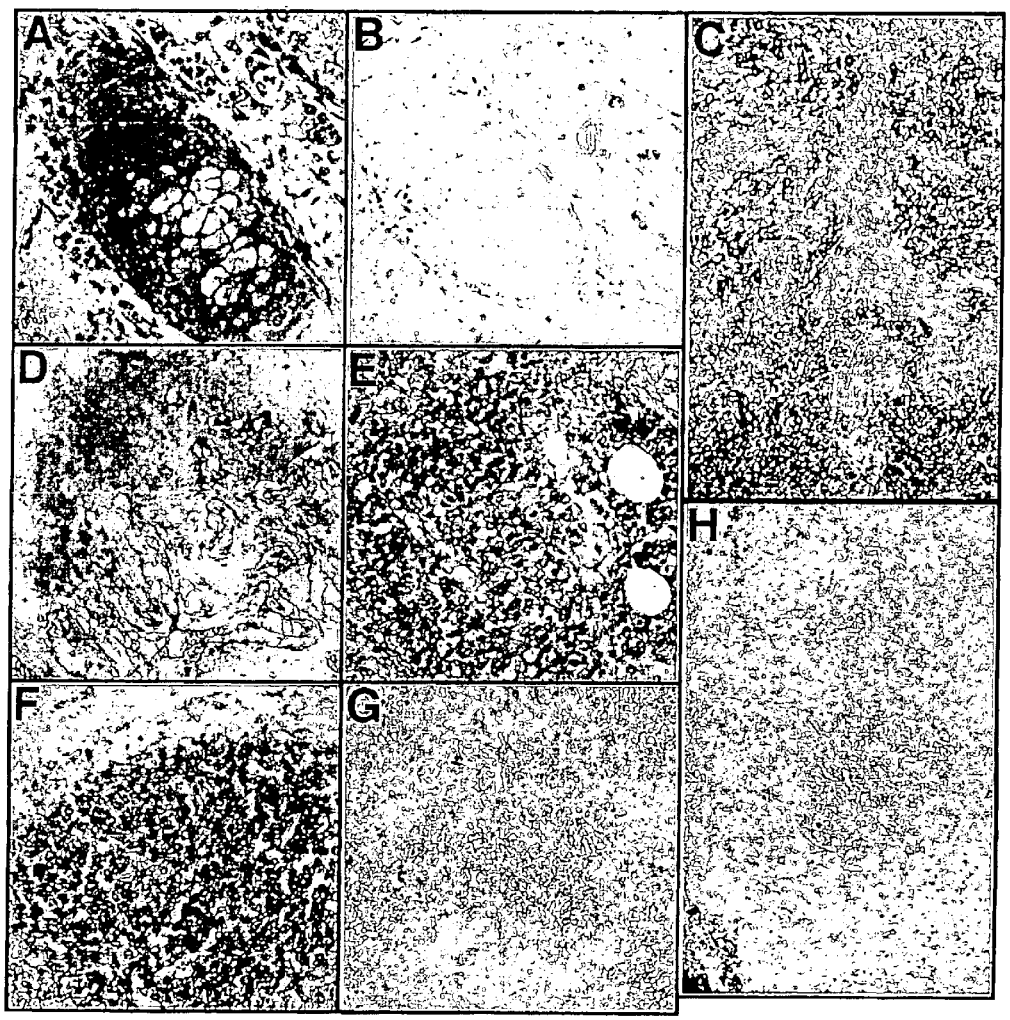
FIG. 1: Tbdn-1 is highly expressed in developing bone and in bone tumors. Adjacent paraffin sections of day 14 gestation mouse embryo ribcage bones were stained using anti-tbdn-1 antibody Ab1272 (A) or preimmune IgY control antibody (B). Paraffin sections of primary human osteosarcoma (C, 200×), primary Ewing's sarcoma (D, 200×; E, 400×) or xenografted human Ewing's tumor cell line EWS-96 (F, 400×) were stained using anti-tbdn-1 antibody or preimmune IgY control antibody (G, Ewing's xenograft, 400×; H, osteosarcoma, 200×). A, B, D, E, F and G were developed with alkaline phosphatase and fast red substrate (red stain) and counterstained with aqueous methyl green. C and H were developed with horseradish peroxidase (reddish-brown stain). Developing bone, both the primary bone tumors, and the xenografted Ewing's cell line showed intense tbdn-1 expression in tumor cells. Tbdn-1 staining was not seen in normal bone tissue (blue/green) surrounding the Ewing's sarcoma tumor (D) or was present at only very low levels in tissue surrounding the Ewing's xenograft (F, yellow-brownish areas, arrowed).

As used herein, the term "biologically active" refers to a protein having structural, regulatory, or biochemical functions of a naturally occurring molecule.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation, or any other process which retains at least one biological function of the polypeptide from which it was derived.

As used herein the term "gene" or "recombinant gene" refers to a nucleic acid comprising an open reading frame encoding tbdn-1, including both exon and (optionally) intron sequences. A "recombinant gene" refers to nucleic acid encoding tbdn-1 and comprising tbdn-1 encoding, exon sequences, though it may optionally include intron sequences which are either derived from a chromosomal tbdn-1 gene or from an unrelated chromosomal gene. The term "intron" refers to a DNA sequence present in a given tbdn-1 gene which is not translated into protein and is generally found between exons.

The words "insertion" or "addition," as used herein, refer to changes in an amino acid or nucleotide sequence resulting in the addition of one or more amino acid residues or nucleotides, respectively, to the sequence found in the naturally occurring molecule.

As used herein, the term "nucleic acid" refers to polynucleotides such as deoxyribonucleic acid (DNA), and, where appropriate, ribonucleic acid (RNA). This term is used interchangeably with the term "oligonucleotide." The term should also be understood to include, as equivalents, analogs of either RNA or DNA made from nucleotide analogs, and, as applicable to the embodiment being described, single-stranded (such as sense or antisense) and double-stranded polynuclectides.

The phrases "percent identity" or "percent homology" refers to the percentage of sequence similarity found in homologues of a particular amino acid or nucleic acid sequence when comparing two or more of the amino acid or nucleic acid sequences.

As used herein, the term "transfection" means the introduction of a nucleic acid, e.g., an expression vector, into a recipient cell by nucleic acid-mediated gene transfer.

"Transformation", as used herein, refers to a process in which a cell's genotype is changed as a result of the cellular uptake of exogenous DNA or RNA, and, for example, the transformed cell expresses a recombinant form of tbdn-1, or where anti-sense expression occurs, from the transferred gene, the expression of a naturally-occurring form of tbdn-1 is disrupted.

The term "tumor" in the following specification denotes an uncontrolled growing mass of abnormal cells. This term includes both primary tumors, which may be benign or malignant, as well as secondary tumors, or metastases which have spread to other sites in the body.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto. Vectors may also be viral vectors wherein the viral vector is selected from the group consisting of a lentivirus, adenovirus, adeno-associated virus and virus-like vectors.

Discussion

The tbdn-1 protein (SEQ. ID. NO. 1) is highly expressed in developing bone and in bone tumors, including Ewing's sarcoma and osteosarcoma (FIG. 1). Postnatal expression of tbdn-1 is restricted to the bone marrow and certain types of vasculature such as ocular and ovarian blood vessels (11). Tbdn-1 is downregulated during IEM capillary formation in vitro. Inhibition of tbdn-1 by expression of antisense tbdn-1 cDNA augments capillary formation of IEM cells.

The in vivo expression pattern of tbdn-1 apparently functions to regulate the growth and development of bone tissue. Tbdn-1 expression is not observed in normal postnatal bone cells. Accordingly, a recombinant antisense construct of tbdn-1 cDNA (tbdn-1 cDNA given by SEQ. ID. NO. 2) has been generated (tbdn-1 cDNA sequence in an antisense orientation) and expressed in both the IEM and bone tumor cell lines. It has been found that this recombinant antisense construct blocks expression of the tbdn-1 protein. Blockage of tbdn-1 expression in Ewing's sarcoma cells using an antisense tbdn-1 cDNA construct (AStbdn-1) inhibits tumor growth in vitro and in vivo as xenografted tumors. These results are consistent with the premise that the tbdn-1 pathway controls growth of Ewing's sarcoma cells and that blockage of the tbdn-1 pathway provides a therapeutic alternative for treatment Ewing's tumors and also for osteosarcomas and bone tumors generally.

Nucleic acids which have a sequence that differs from the nucleotide sequence shown in SEQ ID No. 2 due to degeneracy in the genetic code and having at least 70% sequence homology, are also within the scope of the invention. Such nucleic acids are functionally equivalent to tbdn-1 cDNA (i.e., a cDNA's having a biological activity equivalent to that of cDNA derived from tbdn-1 gene) but differ in sequence due to degeneracy in the genetic code. One skilled in the art will appreciate that these variations in one or more nucleotides of the nucleic acids encoding tbdn-1 protein may exist among individuals of a given species due to natural allelic variation. Any and all such nucleotide variations and resulting amino acid polymorphisms are within the scope of this invention.

Fragments of the tbdn-1 cDNA sequence as well as the entire cDNA of tbdn-1 may be used to generate the antisense nucleotide sequences. The nucleic acid fragments include those capable of producing antisense cDNA constructs which form antisense mRNA's that hybridize under high or low stringency conditions with nucleic acids from other, including alternate isoforms, e.g. mRNA splicing variants.

Antisense oligonucleotides derived from the cDNA of tbdn-1 include single-stranded antisense oligonucleotides that are at least 15 nucleobases in length and preferably at least 25 nucleobases in length. These antisense oligonucleotides hybridize with the native mRNA of tbdn-1 to block expression of tbdn-1. Such oligonucleotides within the scope of the invention may also contain linker sequences, modified restriction endonuclease sites and other sequences useful for molecular cloning, expression or purification of recombinant forms of the subject tbdn-1 protein.

Antisense cDNA molecules include, but are not limited to base pairs of at least 1000 nucleobases, base pairs 1413-1 (SEQ ID NO. 3) and base pairs 3418-1 (SEQ ID NO. 4). The antisense cDNA's within the scope of the invention may also contain linker sequences, modified restriction endonuclease sites and other sequences useful for molecular cloning, expression or purification of recombinant forms of the subject tbdn-1 protein.

Methods of Treatment of Ewings Sarcoma, Osteosarcoma and Related Sarcomas

Invention primarily relates to the use of the isolated oligonucleotides in antisense therapy for the treatment of Ewing's Sarcoma, osteosarcoma and other or related sarcomas expressing high levels of tbdn-1. As used herein, antisense therapy refers to administration or in situ generation of antisense cDNA or oligonucleotides or their derivatives which specifically hybridize (e.g. binds) under low and high stringency conditions, with the native mRNA and/or genomic DNA encoding a tbdn-1 protein, so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy, which relies on specific binding to oligonucleotide sequences.

Absolute complementarity, although preferred, is not required. A sequence complementary to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

An antisense construct of the present invention can be delivered, for example, as an expression plasmid which, when transcribed in the cell, produces RNA, which is complementary to at least a unique portion of the cellular mRNA which encodes a tbdn-1 protein.

Alternatively, the antisense construct can be an oligonucleotide, which is generated ex vivo and which, when introduced into the cell, causes inhibition of expression by hybridizing with the mRNA and/or genomic sequences of an tbdn-1 gene. Such oligonucleotides are preferably modified oligonucleotides, which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of oligonucleotide (see also U.S. Pat. Nos. 5,176,996, 5,294,564 and 5,256,775, which are herein incorporated by reference). Additionally, general approaches to constructing oligomers useful in antisense therapy have been reviewed (13, 14).

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in Remmington's Pharmaceutical Sciences, Meade Publishing Co., Easton, Pa., and may include both human and veterinary formulations. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

In clinical settings, the gene delivery systems for therapeutic tbdn-1 genes can be introduced into a patient (or non-human animal) by any of a number of methods, each of which is known in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors. the pharmaceutical preparation can comprise one or more cells which produce the gene delivery system.

Gene therapy methodologies can also be described by delivery site. Fundamental ways to deliver genes include ex vivo gene transfer, in vivo gene transfer and in vitro gene transfer. In ex vivo gene transfer, cells are taken from the patient and grown in cell culture. The DNA is transfected into the cells, and the transfected cells are expanded in number and then reimplanted in the patient. In in vitro gene transfer, the transformed cells are cells growing in culture, such as tissue culture cells, and not particular cells from a particular patient. These "laboratory cells" are transfected, and the transfected cells are selected and expanded for either implantation into a patient or for other uses. In vivo gene transfer involves introducing the DNA into the cells of the patient when the cells are within the patient. All three of the broad based categories described above may be used to achieve gene transfer in vivo, ex vivo and in vitro.

Mechanical (i.e., physical) methods of DNA delivery can be achieved by microinjection of DNA into germ or somatic cells, pneumatically delivered DNA-coated particles such as the gold particles used in a "gene gun" and inorganic chemical approaches such as calcium phosphate transfection. It has been found that physical injection of plasmid DNA into muscle cells yields a high percentage of cells which are transfected and have sustained marker genes. The plasmid DNA may or may not integrate into the genome of cells. Non-integration of the transfected DNA would allow the transfection and expression of gene product proteins in terminally differentiated, non-proliferative tissues for a prolonged period of time without fear of mutational insertions, deletions or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer may also be employed for injecting DNA into cells, tissues and organs. With a particle bombardment device, or "gene gun," a motive force is generated to accelerate DNA-coated high density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art.

Chemical methods of gene therapy involve carrier-mediated gene transfer through the use of fusogenic lipid vesicles such as liposomes or other vesicles for membrane fusion. A carrier harboring a DNA of interest can be conveniently introduced into body fluids or the bloodstream and then site-specifically directed to the target organ or tissue in the body. Cell or organ-specific DNA-carrying liposomes, for example, can be developed and the foreign DNA carried by the liposome absorbed by those specific cells. Injection of immunoliposomes that are targeted to a specific receptor on certain cells can be used as a convenient method of inserting the DNA into the cells bearing that receptor. Another carrier system that has been used is the asialoglycoprotein/polylysine conjugate system for carrying DNA to hepatocytes for in vivo gene transfer.

Transfected DNA may also be complexed with other kinds of carriers so that the DNA is carried to the recipient cell and then deposited in the cytoplasm or in the nucleoplasm. DNA can be coupled to carrier nuclear proteins in specifically engineered vesicle complexes and carried directly into the nucleus.

Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Biological gene therapy methodologies employ viral vectors to insert genes into host cells. The host cells include, but are not limited to bacterial or eukaryotic cells. Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA completed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells providing that the viral structural proteins are supplied in trans in the packaging cell line.

Fundamental advantages of retroviral vectors for gene transfer include efficient infection and gene expression in most cell types, precise single copy vector integration into target cell chromosomal DNA and ease of manipulation of the retroviral genome. For example, altered retrovirus vectors have been used in ex vivo methods to introduce genes into peripheral and tumor-infiltrating lymphocytes, hepatocytes, epidermal cells, myocytes or other somatic cells (which may then be introduced into the patient to provide the gene product from the inserted DNA).

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell-free virion so injection of producer cell lines are not necessary. Another potential advantage to adenoviral vectors is the ability to achieve long term expression of heterologous genes in vivo.

Viral vectors have also been used to insert genes into cells using in vivo protocols. To direct tissue-specific expression of foreign genes, cis-acting regulatory elements or promoters that are known to be tissue-specific may be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus-infected surrounding cells, in turn, also expressed the gene product. A viral vector can be delivered directly to the in vivo site (by catheter, for example) thus allowing only certain areas to be infected by the virus and providing long-term, site-specific gene expression. In vivo gene transfer using retrovirus vectors has also been demonstrated in mammary tissue and hepatic tissue by injection of the altered virus; into blood vessels leading to the organs.

The compounds of the present invention may also be useful for the prevention of metastases from the tumors described above either when used alone or in combination with radiotherapy and/or other chemotherapeutic treatments conventionally administered to patients for treating angiogenic diseases. For example, when used in the treatment of solid tumors, compounds of the present invention may be administered with chemotherapeutic agents such as alpha inteferon, COMP (cyclophosphamide, vincristine, methotrexate and prednisone), etoposide, mBACOD (methortrexate, bleomycin, doxorubicin, cyclophosphalmide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoireas including carmustine, lomustine, semustine and streptozocin; alkyl sulfonates including busulfan; triazines including dacarbazine; ethyenimines including thiotepa and hexamethylmelamine; folic acid analogs including methotrexate; pyrimidine analogues including 5-fluorouracil, cytosine arabinoside; purine analogs including 6-mercaptopurine and 6-thioguanine; antitumor antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar. For example, a tumor may be treated conventionally with surgery, radiation or chemotherapy and antisense cDNA tbdn-1 administration to stabilize and inhibit the growth of any residual primary tumor.

When used in the above or other treatments, a therapeutically effective amount of one of the compounds of the present invention may be employed in pure form or, where such forms exist, in pharmaceutically acceptable salt form and with or without a pharmaceutically acceptable excipient. A "therapeutically effective amount" of the compound of the invention means a sufficient amount of the compound to limit tumor growth or to slow or block tumor metastasis at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the compound at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose.

Gene therapy also contemplates the production of a protein or polypeptide where the cell has been transformed with a genetic sequence that turns off the naturally occurring gene encoding the protein, i.e., endogenous gene-activation techniques.

EXPERIMENTAL EXAMPLES

Cell Culture

The EWS-96 cell line is derived from a Ewing's sarcoma patient specimen and is obtained at diagnosis. This cell line is cloned using limiting dilution. EWS-96 cell line exhibits MIC2 surface expression as detected by flow cytometry analysis with the anti-MIC2 antibody O13 (Signet Laboratories, Dedham Mass.). The t(11;22) fusion mRNA product is detected in this cell line by RT-PCR. All experiments involving the use of pathological specimens of human tissues in these studies are obtained under informed consent under the approval of the Institutional Review Board of Children's Hospital Medical Center (Cincinnati, Ohio). All research on human specimens follows the tenets of the Declaration of Helsinki at all times. RD-ES and RF/6A cells are obtained from the American Type Culture Collection (Manassas, Va.), while the IEM cell line has been previously described (15). SJES 1, 7, and 8 Ewing's sarcoma cell lines were kindly provided by Dr. Thomas Look at St. Jude Children's Research Hospital (Memphis, Tenn.). All cell lines are grown and maintained in culture in low glucose Dulbecco's Modified Eagle Media (DMEM) supplemented with 2 mM glutamine, and 10% fetal bovine serum (FBS). For RF/6A cells, culture media is further supplemented with 50 uM of non-essential amino acids.

EWS-96 cells are transfected by lipofection with the vector pcDNA3.1/Zeo (Invitrogen, Calif.) alone, or with a construct of the pcDNA3.1/Zeo vector harboring tbdn-1 cDNA nucleotide sequences 1-1413 in an antisense orientation (AStbdn-1). Two days after transfection, cells are selected with 25 ug/ml of Zeocin (Invitrogen, Calif.). After selection, clones are picked with cloning cylinders, expanded and characterized.

Xenograft Tumors

For Ewing's sarcoma xenograft tumors, NOD scid B2m mice (Jackson Laboratory, Bar Harbor Me.) are injected subcutaneously with $5\times10^6$ viable EWS-96 cells (parental or transfected). Cell viability is assessed by trypan blue dye exclusion. Tumor growth of EWS-96 cells is monitored on a daily to weekly basis by measurement using fine calipers. After sacrifice, tumors are carefully dissected and weighed immediately thereafter. Xenograft human osteosarcoma tumors are obtained from the nu/nu mice xenograft bank of the Division of Hematology/Oncology at Children's Hospital Medical Center (Cincinnati, Ohio). Origin of the xenograft osteosarcomas is confirmed by chromosome analysis. All experiments involving animals are performed in accordance with the National Institutes of Health Guidelines on the Care and Use of Laboratory Animals and are approved by the Children's Hospital Medical Center (Cincinnati, Ohio) Institutional Animal Care and use Committee.

Western Blotting

Cell lysates are prepared using Triton-X 100 lysis buffer (50 mM Tris, pH 8.0, 150 mM NaCl, 1% Triton-X 100) supplemented with protease inhibitors (1 mM PMSF, 0.3 U/ml aprotinin, and 10 ug/ml leupeptin) and phosphatase inhibitors (1 mM sodium orthovanadate, 25 mM sodium fluoride, and 10 mM betaglycerophosphate. Lysates are clarified by centrifugation and protein is quantified and analyzed by SDS-PAGE. Gels are processed for western blotting using antibodies directed against FLI-1 (Santa Cruz Biotechnology, Calif.) and tbdn-1 (Ab1272, ref. 22). Incubations, washes and western blotting are performed by standard procedures using chemiluminescence detection (ECL Plus reagent, Amersham).

Northern Blotting

Northern blotting is performed as previously described (Sambrook et al., 1989). Blots are hybridized with a $^{32}$P-labeled 5'end fragment of the tbdn-1 cDNA (nucleotides 1–1413) as probe. Blots are reprobed with a mouse 18S ribosomal RNA cDNA in order to confirm loading equivalency and RNA integrity.

Immunocytochemistry

Immunocytochemistry is performed on paraformaldehyde fixed, paraffin embedded sections of mouse and human tissue specimens to detect tbdn-1. Some sections are incubated in a solution of methanol/peroxide to quench endogenous peroxidase activity in cases of peroxidase substrate reactions. Following a 1 hour blocking step in 2% normal goat serum, sections are incubated with either a 1/100 dilution of anti-tbdn-1 antibody Ab1272 or preimmune IgY. After rinsing in PBS, reactions are developed using the appropriate peroxidase or alkaline phosphatase conjugated species specific secondary antibodies (Promega, Madison, Wis.). Red color reactions are generated using amino ethylcarbazole substrate (AEC, Sigma) in the presence of $H_2O_2$ for peroxidase reactions or naphthol-AS-MX Phosphate in the presence of Fast Red and Levamisole (to block endogenous tissue alkaline phosphatase activity) for alkaline phosphatase reactions. Peroxidase reacted sections are mounted in Cytoseal-60 (Stephens Scientific). Alkaline phosphatase reacted sections are counterstained using a 0.5% aqueous solution of methyl green, rinsed in water, dried and finally mounted in Permount (Fisher, Pittsburgh, Pa.). Sections are viewed and photographed using a Nikon microscope system with a Kodak DC120 digital camera attachment.

In vitro Transcription and Translation

In vitro transcription and translation of the various constructs with the T7 TNT-coupled rabbit reticulocyte lysate system (Promega) are carried out according to the manufacturer's procedure in the presence of [$^{35}$S]methionine/[$^{35}$S]cysteine (1175 Ci/mmol; NEN Life Science Products, Boston, Mass.). Samples are analyzed by SDS-PAGE and autoradiography.

In vitro Growth Assays

Parental and transfected EWS-96 cell clones are plated at $1\times10^5$, $2.5\times10^5$ and $5\times10^5$ cells per 35 mm dish in standard culture media and cultured for 72, 48 and 24 hours, respectively. After culturing, cells are trypsinized and the number of viable cells per dish is determined in triplicate samples using trypan blue dye exclusion. For growth in soft agar, $2\times10^5$ parental or transfected EWS-96 cells are plated into a 60 mm dish in 2 ml of 0.33% Agar Noble (Difco Laboratories) in complete culture media over a layer of 2 ml of 0.5% Agar Noble in complete media. Between 7 to 10 days after plating, colonies growing in soft agar are counted.

Results

Figure 2:
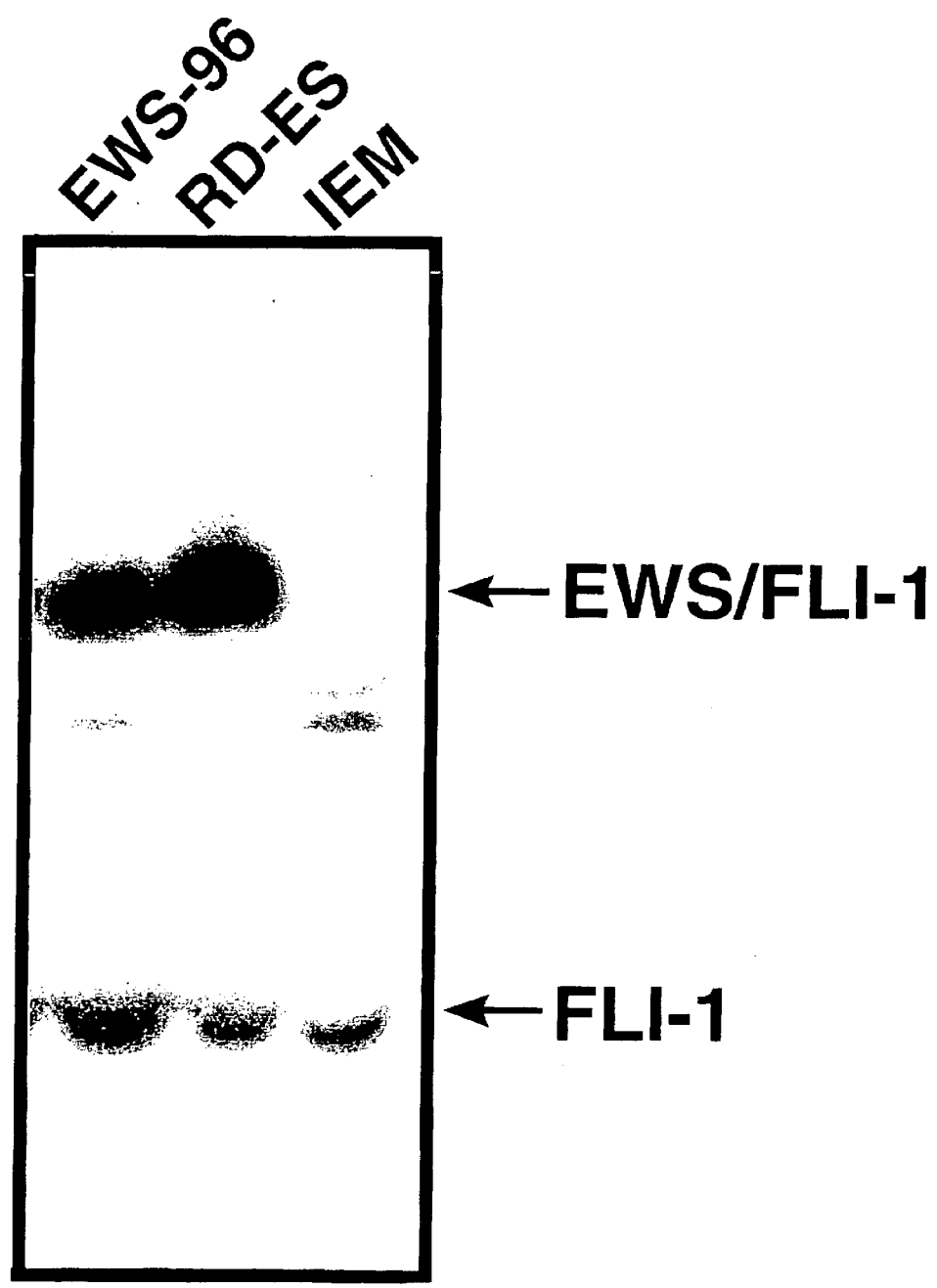
FIG. 2: The EWS/FLI-1 fusion protein is expressed in Ewing's sarcoma cell lines. Western blotting was performed on protein lysates of the indicated cell lines using an antibody to FLI-1 (14). FLI-1, which is expressed by the IEM embryonic endothelial cell line and both the EWS-96 and RD-ES Ewing's sarcoma cell lines, is indicated. The EWS/FLI-1 fusion protein, resolving as the larger molecular weight band indicated on the blot, is expressed only in the Ewing's sarcoma cell lines and not in the endothelial cell line.
Figure 3:
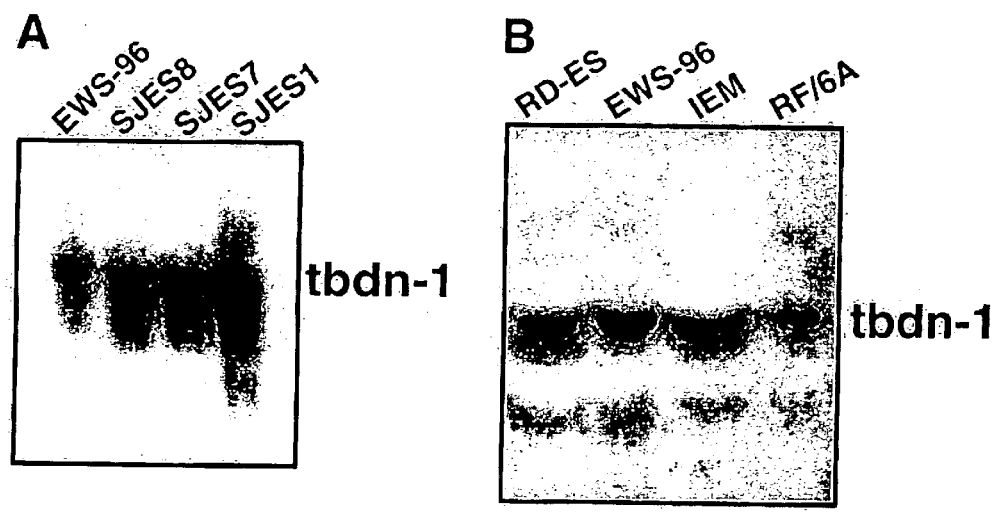
FIG. 3: Tbdn-1 transcript and protein are highly expressed in Ewing's sarcoma cell lines. A, Northern blot analysis of RNA prepared from Ewing's sarcoma cell lines EWS-96, SJES8, SJES7 and SJES1 as indicated, was performed using a tbdn-1 cDNA probe. B, Western blot analysis of protein lysates of embryonic and retinal endothelial cell lines (IEM and RF/6A, respectively) and Ewing's sarcoma cell lines (RD-ES and EWS-96) was performed using the anti-tbdn-1 antibody Ab1272 revealing the 69 kDa band corresponding to tbdn-1.

The EWS-96 cell line expresses the hallmark EWS/FLI-1 fusion protein (FIG. 2) characteristic of Ewing's sarcoma. The EWS/FLI-1 fusion protein expressed by the EWS-96 cell line co-migrates with the EWS/FLI-1 type II fusion protein expressed by the Ewing's sarcoma cell line RD-ES (FIG. 2). All Ewing's sarcoma cell lines examined are positive for tbdn-1 transcript and/or protein (FIG. 3).

Figure 4:
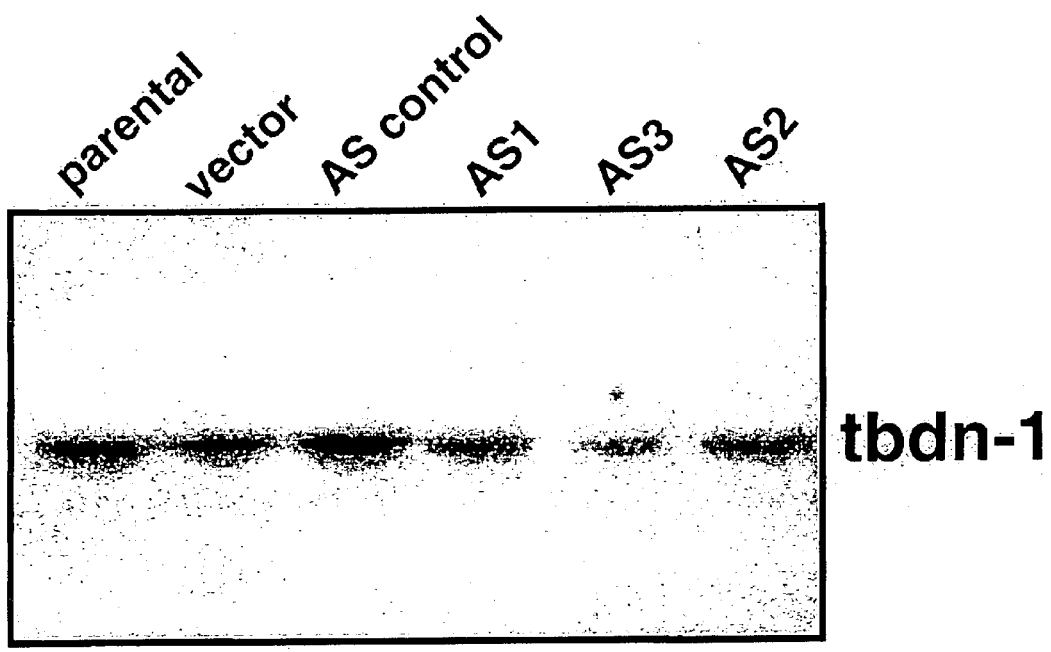
FIG. 4: Inhibition of tbdn-1 expression in Ewing's sarcoma cells using an antisense tbdn-1 construct. Anti-tbdn-1 (Ab1272) western blot analysis of EWS-96 Ewing's sarcoma cell clones stably over-expressing antisense tbdn-1 cDNA (AStbdn-1) show decreased expression of tbdn-1 protein (AS1, AS2 and AS3) compared to controls (parental, parental EWS-96 cells; vector, EWS-96 cells expressing the empty vector; AS control, EWS-96 cells transfected with AStbdn-1 construct but showing no decrease in tbdn-1 expression).
Figure 5:
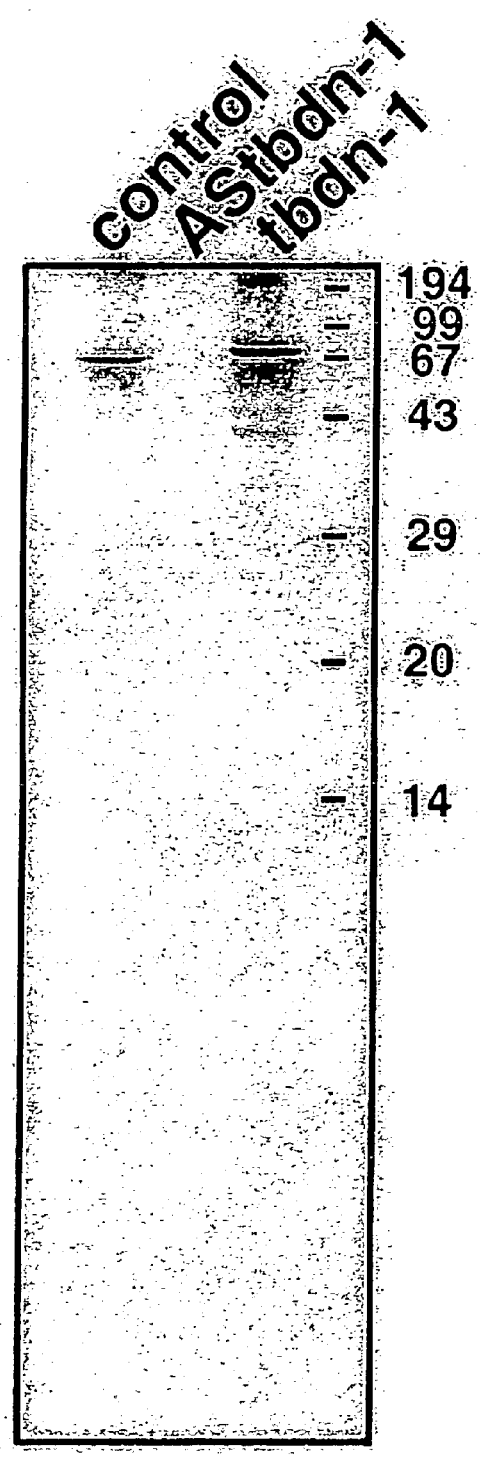
FIG. 5: The antisense tbdn-1 construct AStbdn-1 does not produce aberrant toxic proteins. In vitro protein translated from control (control), antisense tbdn-1 (AStbdn-1) or tbdn-1 (tbdn-1) constructs using $[^{35}S]$ methionine/cysteine were separated on SDS-PAGE and analyzed by autoradiography. In control preparations, one major band of ~61 kDa is observed, while the tbdn-1 construct leads to synthesis of one major ~69 kDa band as expected. No protein is synthesized using the antisense tbdn-1 construct (Astbdn-1). Apparent molecular weight markers are indicated to the right of the gel.

To address the functional role of tbdn-1 in Ewing's sarcoma, clones of Ewing's sarcoma cells are generated by stably over-expressing antisense tbdn-1 cDNA fragment (AStbdn-1) in order to block tbdn-1 expression. The AStbdn-1 construct does not encode an irrelevant protein product which could be nonspecifically toxic to the Ewing's sarcoma cells (FIG. 4). Western blot analysis revealed that several Ewing's sarcoma cell clones transfected with the AStbdn-1 construct exhibited reduced expression of tbdn-1 protein expression when compared to the parental cells or Ewing's sarcoma cell clones expressing the empty vector (FIG. 5, and data not shown).

The effect of downregulation of tbdn-1 expression was examined on both in vitro and in vivo growth of the Ewing's sarcoma cells. The in vitro growth (under standard culture conditions) and the anchorage independent growth in soft agar of clones of Ewing's sarcoma cells exhibiting reduced levels of tbdn-1 expression is significantly reduced compared to control cells (parental cells, cells transfected with the vector alone or with the AStbdn-1 construct but showing no reduction in tbdn-1 levels [FIG. 5]) (FIGS. 6A and B, respectively).

Figure 6:
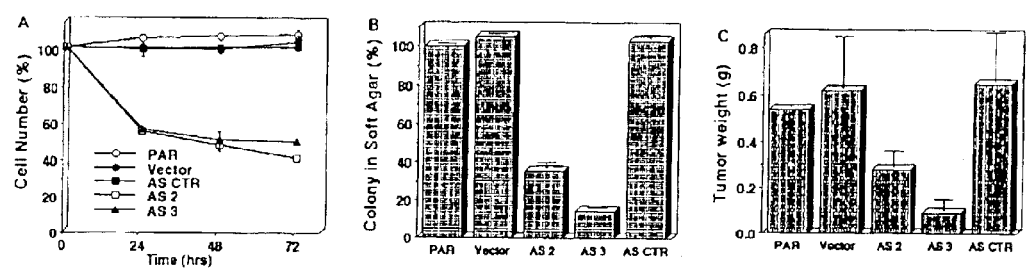
FIG. 6: Inhibition of tbdn-1 expression suppresses Ewing's sarcoma tumor cell growth. Ewing's sarcoma cell (EWS-96) clones showing decreased expression of tbdn-1 (AS 2 and AS 3) exhibit reduced growth compared to controls (PAR, parental EWS-96 cells; Vector, EWS-96 cells expressing the empty vector; AS CTR, EWS-96 cells transfected with AStbdn-1 construct but showing no decrease in tbdn-1 expression). Growth of EWS-96 cells were assayed in standard culture conditions (A), in soft agar (B), and as xenograft tumors (C). Values are expressed +/− SEM.

Furthermore, the downregulation of tbdn-1 expression in Ewing's sarcoma cells greatly inhibits their growth as tumors in vivo in a xenograft model compared to the control clones (FIG. 6C). The levels of tbdn-1 expressed by the different EWS-96 clones (parental, transfected with the vector alone or AStbdn-1) correlates with their rate of growth in soft agar and as xenografts (FIGS. 5, 6B and C). EWS-96 clone AS3 which expresses the lowest level of tbdn-1 (FIG. 5) exhibited the most reduced growth rate in soft agar and as xenograft tumors (FIGS. 6B and C). EWS-96 clone AS2, which expresses intermediate levels of tbdn-1 (more than clone AS3 but less than controls, FIG. 5) exhibits intermediate growth rates (higher than clone AS3 but less than controls) in soft agar and as xenograft tumors (FIGS. 6B and C).

References (1) Boring, C. C., Squires, T. S., Tong, T., and Montgomery. S. Cancer statistics, 1994, CA Cancer J. Clin., 44; 7–26, 1994.

(2) Hudson, M., Jaffe, M. R., and Jaffe, N. Pediatric osteosarcoma: therapeutic strategies, results, and prognostic actors derived from a 10-year experience. J. Clin. Oncol., 8: 1988–1997, 1990.

(3) Link, M. P., Goorin, A. M., Mixer, A. W., Link, M. P., Goorin, A. M., Miser, A. W., Green, A. A., Pratt C. H., Belasco, J. B., Pritchard, J., Malpas, J. S., Baker, A. R., Kirkpatrick, J. A., Ayala, A. O., Schuster, J. J., Abelson, H. T., Simone, J. V., and Vietti, T. J. The effect of adjuvant chemotherapy on relapse-free survival in patients with osteosarcoma of the extremity. N. Engl. J. Med, 314: 1600–1602, 1991.

(4) Goorin, A. M., Perez-Atayde, A., Gebbhardt, M., et al. Weekly high-dose methotrexate and doxorubicin for osteosarcoma: the Dunn-Farber Cancer Institute/The Children's Hospital-Study III. J. Clin. Oncol., 5: 1178–1184, 1987.

(5) Kane, M. J. Chemotherapy of advanced soft tissue and osteosarcoma. Semin. Oncol., 16:297–304, 1989.

(6) Palumbo, J. S., and Zwerdling, T. Soft tissue sarcomas of infancy. Semin. Perinatol., 23: 299–309, 1999.

(7) Fizazi, K., Dohollou, N., Blay, J. Y., Guerin, S., Le Cesne, A., Andre, F., Pouillart, P., Tursz, T., and Nguyen, B. B. Ewing's family of tumors in adults: multivariate analysis of survival and long-term results of multimodality therapy in 182 patients. J. Clin. Oncol., 16: 3736–3743, 1998.

(8) Arndt, C. A., and Crist, W. M. Common musculoskeletal tumors of childhood and adolescence. N. Engl. J. Med., 341: 342–352, 1999.

(9) West, D. C. Ewing sarcoma family of tumors. Curr, Opin, Oncol., 12: 323–329, 2000.

(10) de Alava, E, and Gerald, W. L. Molecular biology of the Ewing's sarcoma/primitive neuroectodermal tumor family. J. Clin. Oncol., 18: 204–213, 2000.

(11) Gendron, R. L., Adams, L. C., and Paradis, H. Tubedown-1, a novel acetyltransferase associated with blood vessel development. Dev. Dyn., 218: 300–315, 2000.

(12) Sambook, J., Fritsch, E. F., and Maniatis, T. Molecular Cloning, A Laboratory Manual. 2nd, Cold Spring Harbor Laboratory Press (eds.), New York, 1989.

(13) van der Krol et al. Modulation of Eukaryopic Gene Expression by Complimentary RNA or DNA Sequences, Biotechniques 6:958–976, 1988.

(14) Stein et al. Oligodeoxynucleotides as Inhibitors of Gene Expressnion: a Review, Cancer Res. 48:2659–2668, 1988.

(15) Gendron, R. L., Tsai, F. Y., Paradis, H., Arceci, R. J. 1996, Induction of Embryonic Vasculogenesis by bFGF and LIF in vitro and in vivo. Dev. Biol. 177: 332–346.

What is claimed is:

1. An isolated nucleic acid molecule consisting of the sequence shown in SEQ ID NO. 2.

2. The isolated nucleic acid molecule of claim 1, wherein the amino acid sequence is expressed in Ewing's Sarcoma family of tumors.

3. The isolated nucleic acid molecule of claim 1, wherein the amino acid sequence is expressed in osteosarcoma tumors.

4. The isolated nucleic acid molecule of claim 1, wherein said molecule is a single-stranded cDNA molecule.

5. The isolated nucleic acid molecule of claim 4, wherein said molecule is biologically active.

6. An isolated nucleic acid molecule consisting of the sequence shown in SEQ ID NO. 2, wherein said molecule is a biologically active, single stranded cDNA molecule, wherein said molecule or fragment thereof is used to generate a first antisense nucleic acid molecule to the sequence shown in SEQ ID No. 2, wherein said first antisense acid molecule consists of the sequence shown in SEQ ID No. 3.

7. An isolated nucleic acid molecule consisting of the sequence shown in SEQ ID NO. 2, wherein said molecule is a biologically active, single stranded cDNA molecule, wherein said molecule or fragment thereof is used to generate a second antisense nucleic acid molecule of the sequence shown in SEQ ID No. 2, wherein the second antisense nucleuc acid molecule consists of the sequence shown in SEQ ID No. 4.

8. A composition comprising the isolated first antisense nucleuc acid molecule shown in SEQ ID No. 3 in an amount effective to limit growth or metastasis of tumor cells expressing the tbdn-1 protein molecule when administered to said tumor cells.

9. The composition of claim 8, additionally comprising a vector selected from the group consisting of viral, plasmid, and mixturs thereof.

10. The composition of claim 8, wherein said tumor cells comprise Ewing's Sarcoma family of tumors or osteosarcoma tumors.

11. A composition comprising the isolated second antisense nucleic acid molecule shown in SEQ ID No. 4 in an amount effective to limit the growth or metastasis of tumor expressing the tbdn-1 protein molecule when administered to said tumor cells.

12. The composition of claim 11, additionally comprising a vector selected from the group consisting of viral, plasmid, and mixtures thereof.

13. The composition of claim 11, wherein said tumor cells comprise Ewing's Sarcoma family of tumors or osteosarcoma tumors.

* * * * *

SEQUENCE LISTING

<160> NUMBER OF SEQ ID NOS: 4

<210> SEQ ID NO 1
<211> LENGTH: 593
<212> TYPE: PRT
<213> ORGANISM: Homo sapiens

<400> SEQUENCE: 1

```
Met Leu Glu Arg Leu Lys Ile Tyr Glu Glu Ala Trp Thr Lys Tyr Pro
1               5                   10                  15

Arg Gly Leu Val Pro Arg Lys Leu Pro Leu Asn Phe Leu Ser Gly Glu
            20                  25                  30

Lys Phe Lys Glu Cys Leu Asp Arg Phe Leu Arg Met Asn Phe Ser Lys
        35                  40                  45

Gly Cys Pro Pro Val Phe Asn Thr Leu Arg Ser Leu Tyr Arg Asp Lys
    50                  55                  60

Glu Lys Val Ala Ile Val Glu Glu Leu Val Val Gly Tyr Glu Thr Ser
65                  70                  75                  80

Leu Lys Ser Cys Arg Leu Phe Asn Pro Asn Asp Asp Gly Lys Glu Glu
                85                  90                  95

Pro Pro Thr Thr Leu Leu Trp Val Gln Tyr Tyr Leu Ala Gln His Tyr
            100                 105                 110

Asp Lys Ile Gly Gln Pro Ser Ile Ala Leu Glu Tyr Ile Asn Thr Ala
        115                 120                 125

Ile Glu Ser Thr Pro Thr Leu Ile Glu Leu Phe Leu Val Lys Ala Lys
    130                 135                 140

Ile Tyr Lys His Ala Gly Asn Ile Lys Glu Ala Ala Arg Trp Met Asp
145                 150                 155                 160

Glu Ala Gln Ala Leu Asp Thr Ala Asp Arg Phe Ile Asn Ser Lys Cys
                165                 170                 175

Ala Lys Tyr Met Leu Lys Ala Asn Leu Ile Lys Glu Ala Glu Glu Met
            180                 185                 190

Cys Ser Lys Phe Thr Arg Glu Gly Thr Ser Ala Val Glu Asn Leu Asn
        195                 200                 205

Glu Met Gln Cys Met Trp Phe Gln Thr Glu Cys Ala Gln Ala Tyr Lys
    210                 215                 220

Ala Met Asn Lys Phe Gly Glu Ala Leu Lys Lys Cys His Glu Ile Glu
225                 230                 235                 240

Arg His Phe Ile Glu Ile Thr Asp Asp Gln Phe Asp Phe His Thr Tyr
                245                 250                 255

Cys Met Arg Lys Ile Thr Leu Arg Ser Tyr Val Asp Leu Leu Lys Leu
            260                 265                 270

Glu Asp Val Leu Arg Gln His Pro Phe Tyr Phe Lys Ala Ala Arg Ile
        275                 280                 285

Ala Ile Glu Ile Tyr Leu Lys Leu His Asp Asn Pro Leu Thr Asp Glu
    290                 295                 300

Asn Lys Glu His Glu Ala Asp Thr Ala Asn Met Ser Asp Lys Glu Leu
305                 310                 315                 320

Lys Lys Leu Arg Asn Lys Gln Arg Arg Ala Gln Lys Ala Gln Ile
                325                 330                 335

Glu Glu Glu Lys Lys Asn Ala Glu Lys Glu Lys Pro Gln Arg Asn Pro
            340                 345                 350

Lys Lys Lys Lys Asp Asp Asp Glu Glu Ile Gly Gly Pro Lys Glu
```

-continued

```
                355                 360                 365
Glu Leu Ile Pro Glu Lys Leu Ala Lys Val Thr Pro Leu Glu Glu
            370                 375                 380

Ala Ile Lys Phe Leu Thr Pro Leu Lys Asn Leu Val Lys Asn Lys Ile
385                 390                 395                 400

Glu Thr His Leu Phe Ala Phe Glu Ile Tyr Phe Arg Lys Glu Lys Phe
                405                 410                 415

Leu Leu Met Leu Gln Ser Val Lys Arg Ala Phe Ala Ile Asp Ser Ser
            420                 425                 430

His Pro Trp Leu His Glu Cys Met Ile Arg Leu Phe His Ser Val Cys
            435                 440                 445

Glu Ser Lys Asp Leu Pro Glu Thr Val Arg Thr Val Leu Lys Gln Glu
            450                 455                 460

Met Asn Arg Leu Phe Gly Ala Thr Asn Pro Lys Asn Phe Asn Glu Thr
465                 470                 475                 480

Phe Leu Lys Arg Asn Ser Asp Ser Leu Pro His Arg Leu Ser Ala Ala
                485                 490                 495

Lys Met Val Tyr Tyr Leu Asp Ser Ser Ser Gln Lys Arg Ala Ile Glu
            500                 505                 510

Leu Ala Thr Thr Leu Asp Gly Ser Leu Thr Asn Arg Asn Leu Gln Thr
            515                 520                 525

Cys Met Glu Val Leu Glu Ala Leu Cys Asp Gly Ser Leu Arg Asp Cys
530                 535                 540

Lys Glu Ala Ala Glu Ala Tyr Arg Ala Ser Cys His Lys Leu Phe Pro
545                 550                 555                 560

Tyr Ala Leu Ala Phe Met Pro Pro Gly Tyr Glu Glu Asp Met Lys Ile
                565                 570                 575

Thr Val Asn Gly Asp Ser Ser Ala Glu Thr Glu Glu Leu Ala Asn Glu
            580                 585                 590

Ile
```

<210> SEQ ID NO 2
<211> LENGTH: 3418
<212> TYPE: DNA
<213> ORGANISM: Homo sapiens

<400> SEQUENCE: 2

```
caagtaacac ccgcaagatg atagaggatc tgcagagtga gcatcatgga ttggttatgc      60
tttaccattt attagaagac tatgaaatgg cagcaaaaat tttagaagag tttaggaaaa     120
cacagcagac atctcctgat aaagtggatt atgaatatag tgaactcctc ttatatcaga     180
atcaagttct tcgggaagca ggtctttata gagaagccct ggaacatctt tgtacctatg     240
aaaagcagat ttgtgataaa cttgctgttg aagaaaccaa aggggaactt ctgttgcagt     300
tgtgtcgttt ggaagatgct gctgacgttt atagaggatt acaagagagg aatcctgaaa     360
attgggccta ttacaaggc ttagaaaaag cactgaagcc agctaatatg ttagaacggc      420
taaaatata tgaggaagcc tggactaaat accccagggg actcgtgcca agaaagctgc      480
ccttaaactt tttatctgga gagaagttta aggagtgttt ggataggttc ctaaggatga     540
atttcagcaa gggctgtcca cctgtcttca ataccttgag gtctttatac agagataaag     600
agaaggtggc aatcgtagaa gaactagtag ttggttatga acttctctct aaaagttgtc     660
gcctatttaa ccccaatgat gatggaaagg aggaacctcc aaccacatta ctttgggtcc     720
agtactattt ggcacagcat tatgataaaa ttggtcagcc atccattgct ctggaataca     780
```

-continued

```
taaatactgc aattgaaagt acaccaacat tgatagaact ctttcttgta aaagctaaaa      840
tctataagca tgctgggaat attaaagaag ctgccaggtg gatggatgaa gcccaggccc      900
tggacacagc agacagattt attaattcca agtgtgcaaa atacatgtta aaagccaacc      960
tgattaaaga ggctgaagaa atgtgttcca agtttacgag ggaaggaact tcagcggtag     1020
agaacctgaa tgaaatgcag tgtatgtggt tccagacaga gtgtgctcag gcatacaaag     1080
caatgaacaa atttggtgaa gcacttaaga aatgtcatga aattgagaga catttttatag    1140
aaatcaccga tgaccagttt gactttcata catactgtat gaggaagatc acccttagat     1200
catatgtgga cttattaaaa ctagaagatg tacttcgaca gcatccattt tacttcaaag     1260
cagcgagaat tgctattgag atctatttga agcttcatga caaccctctg acagatgaga     1320
acaaagaaca cgaggctgat acagcaaaca tgtctgacaa agagctaaag aaactgcgta     1380
ataaacaaag aagagctcaa aagaaagccc agattgaaga agagaaaaaa aatgccgaaa     1440
aagaaaagcc gcaacggaat ccgaaaaaga aaaggatga tgatgacgaa gaaattggag      1500
gccccaaaga agagcttatc cctgagaaac tggccaaggt tgaaactcca ttggaagaag     1560
ctattaagtt tttaacacca ttgaagaact tggtgaagaa caagatagaa actcatcttt     1620
ttgcctttga gatctacttt aggaaagaaa agtttctttt gatgctacaa tcagtaaagc     1680
gggcatttgc tattgattct agtcatccct ggcttcatga gtgcatgatt cgactctttc     1740
attctgtgtg tgaaagtaaa gacttacccg aaacagttag aacagtatta aaacaagaaa     1800
tgaatcgtct ttttggagca acaaatccaa agaattttaa tgaaaccttt ctgaaaagga     1860
attctgattc attgccacat agattatcag ctgccaaaat ggtatattat ttagattctt     1920
ctagtcaaaa acgagcaata gagctggcga caacacttga tggatccctc accaacagaa     1980
accttcagac ttgcatggaa gtgttggaag ccttgtgtga tggtagccta cgagactgta     2040
aagaagctgc cgaagcctac agagcaagtt gtcataagct tttcccttat gctttggctt     2100
tcatgcctcc tggatacgaa gaggatatga agatcacagt gaacggagat agttctgcag     2160
aaacggaaga actggccaat gaaatctgaa catcattaaa caagcaaatg gaatgacttt     2220
ggaccatatc tagtgtataa tattttgtc acgcacctgc tgcattgctc ttacttacac      2280
agaatgagag gagtaaatgt tcttgccttc aaatagtctt acgtttttta tcctgctgaa     2340
aactatatat aaaatatcta acattacagg atataggttc agtttcttaa aaaattaaaa    2400
gctgctaaaa ttgagggggtt taaaagaaaa aaaaatccgt atcctattcc taccttccct    2460
tcccatgttt ttaactaatt tatataaaat ctggaggcta taacagctaa catagcaggt    2520
gtgtggcaga aatattactt taaatttgtc ttgtgagatt ttgctatatc tcagacagca    2580
taaataaatg ctgttttagc actggattct ttcactgagc acaaagagtt gttggggctt    2640
tagcatctgc ctgattctgt tacggggttg gtgattgacc ataggaagta tgcaatgtga    2700
atcactgtgt acagagccgt ctacaacaca tgcttgacgt tgtagagact gggacacata    2760
gctaccaagc ggattaagtg aaacctagaa ggtgttcagt acgtgtgttg tgtttccaaa    2820
attcactgta catgatcagt ttggtgttct tgtaccacag ttttttaaccg aaggaaccag   2880
ttggaacaat ctcaatttaa ctaaaacttg aagaactaaa ataacaatgc aaaccttttat   2940
cattgttttg gccaaacttg ttaaaactgt aatgcaagaa ccaaatgcac tgtgatgtgg    3000
caccaactaa ttatgcaagc atgaattttt cacctgagag tgaaaaaaga aaactctacc    3060
atggcttgaa gttacaggag cagaactcct gactaccatt ctatgactga tgaagagact    3120
```

-continued

| | |
|---|---|
| aatatctaaa acctcagcag gccttgttca cgatatgcag aaaaagtgct gcagtttaga | 3180 |
| tacctctggg aacttttcca cagtgtcaca ggtttgtaat acttgaagcc cttcatttct | 3240 |
| aagaatatat ttctcgctca gttgtttcag gcaagcccaa gactttgtaa ttttaaagg | 3300 |
| gcccaagatt ttttttcaa taacagacca gcttcttttt cctgcagtta caaatgtaat | 3360 |
| ttctttttt ttttgttgtc aaacataagg taccaaatat gcataaaatt gttttggg | 3418 |

<210> SEQ ID NO 3
<211> LENGTH: 1413
<212> TYPE: DNA
<213> ORGANISM: Homo sapiens

<400> SEQUENCE: 3

| | |
|---|---|
| tctgggcttt cttttgagct cttctttgtt tattacgcag tttctttagc tctttgtcag | 60 |
| acatgtttgc tgtatcagcc tcgtgttctt tgttctcatc tgtcagaggg ttgtcatgaa | 120 |
| gcttcaaata gatctcaata gcaattctcg ctgctttgaa gtaaaatgga tgctgtcgaa | 180 |
| gtacatcttc tagttttaat aagtccacat atgatctaag ggtgatcttc ctcatacagt | 240 |
| atgtatgaaa gtcaaactgg tcatcggtga tttctataaa atgtctctca atttcatgac | 300 |
| atttcttaag tgcttcacca aatttgttca ttgctttgta tgcctgagca cactctgtct | 360 |
| ggaaccacat acactgcatt tcattcaggt tctctaccgc tgaagttcct tccctcgtaa | 420 |
| acttggaaca catttcttca gcctctttaa tcaggttggc ttttaacatg tattttgcac | 480 |
| acttggaatt aataaatctg tctgctgtgt ccagggcctg gcttcatcc atccacctgg | 540 |
| cagcttcttt aatattccca gcatgcttat agattttagc ttttacaaga aagagttcta | 600 |
| tcaatgttgg tgtactttca attgcagtat ttatgtattc cagagcaatg gatggctgac | 660 |
| caatttatc ataatgctgt gccaaatagt actggaccca agtaatgtg ttggaggtt | 720 |
| cctccttcc atcatcattg gggttaaata ggcgacaact ttagagaa gtttcataac | 780 |
| caactactag ttcttctacg attgccacct tctctttatc tctgtataaa gacctcaagg | 840 |
| tattgaagac aggtggacag cccttgctga aattcatcct taggaaccta tccaaacact | 900 |
| ccttaaactt ctctccagat aaaaagttta agggcagctt tcttggcacg agtcccctgg | 960 |
| ggtatttagt ccaggcttcc tcatatattt ttagccgttc taacatatta gctggcttca | 1020 |
| gtgcttttc taagcctttg taataggccc aattttcagg attcctctct tgtaatcctc | 1080 |
| tataaacgtc agcagcatct tccaaacgac acaactgcaa cagaagttcc cctttggttt | 1140 |
| cttcaacagc aagtttatca caaatctgct tttcataggt acaaagatgt tccagggctt | 1200 |
| ctctataaag acctgcttcc cgaagaactt gattctgata taagaggagt tcactatatt | 1260 |
| cataatccac tttatcagga gatgtctgct gtgttttcct aaactcttct aaaatttttg | 1320 |
| ctgccatttc atagtcttct aataaatggt aaagcataac caatccatga tgctcactct | 1380 |
| gcagatcctc tatcatcttg cgggtgttac ttg | 1413 |

<210> SEQ ID NO 4
<211> LENGTH: 3418
<212> TYPE: DNA
<213> ORGANISM: Homo sapiens

<400> SEQUENCE: 4

| | |
|---|---|
| cccaaaacaa tttattgcat atttggtacc ttatgtttga caacaaaaaa aaaaagaaat | 60 |
| tacatttgta actgcaggaa aaagaagctg gtctgttatt gaaaaaaaaa tcttgggccc | 120 |
| tttaaaaatt acaaagtctt gggcttgcct gaaacaactg agcgagaaat atattcttag | 180 |

```
aaatgaaggg cttcaagtat tacaaacctg tgacactgtg gaaaagttcc cagaggtatc    240
taaactgcag cacttttct gcatatcgtg aacaaggcct gctgaggttt tagatattag    300
tctcttcatc agtcatagaa tggtagtcag gagttctgct cctgtaactt caagccatgg    360
tagagttttc tttttcact ctcaggtgaa aaattcatgc ttgcataatt agttggtgcc    420
acatcacagt gcatttggtt cttgcattac agttttaaca agtttggcca aaacaatgat    480
aaaggtttgc attgttattt tagttcttca agttttagtt aaattgagat tgttccaact    540
ggttccttcg gttaaaaact gtggtacaag aacaccaaac tgatcatgta cagtgaattt    600
tggaaacaca acacacgtac tgaacacctt ctaggtttca cttaatccgc ttggtagcta    660
tgtgtcccag tctctacaac gtcaagcatg tgttgtagac ggctctgtac acagtgattc    720
acattgcata cttcctatgg tcaatcacca accccgtaac agaatcaggc agatgctaaa    780
gccccaacaa ctctttgtgc tcagtgaaag aatccagtgc taaaacagca tttatttatg    840
ctgtctgaga tatagcaaaa tctcacaaga caaatttaaa gtaatatttc tgccacacac    900
ctgctatgtt agctgttata gcctccagat tttatataaa ttagttaaaa acatgggaag    960
ggaaggtagg aataggatac ggattttttt ttctttaaaa cccctcaatt ttagcagctt    1020
ttaatttttt aagaaactga acctatatcc tgtaatgtta gatattttat atatagtttt    1080
cagcaggata aaaacgtaa gactatttga aggcaagaac atttactcct ctcattctgt    1140
gtaagtaaga gcaatgcagc aggtgcgtga caaaaatatt atacactaga tatggtccaa    1200
agtcattcca tttgcttgtt taatgatgtt cagatttcat tggccagttc ttccgtttct    1260
gcagaactat ctccgttcac tgtgatcttc atatcctctt cgtatccagg aggcatgaaa    1320
gccaaagcat aagggaaaag cttatgacaa cttgctctgt aggcttcggc agcttcttta    1380
cagtctcgta ggctaccatc acacaaggct tccaacactt ccatgcaagt ctgaaggttt    1440
ctgttggtga gggatccatc aagtgttgtc gccagctcta ttgctcgttt ttgactagaa    1500
gaatctaaat aatataccat tttggcagct gataatctat gtggcaatga atcagaattc    1560
cttttcagaa aggtttcatt aaaattcttt ggatttgttg ctccaaaaag acgattcatt    1620
tcttgtttta atactgttct aactgtttcg ggtaagtctt tactttcaca cacagaatga    1680
aagagtcgaa tcatgcactc atgaagccag ggatgactag aatcaatagc aaatgcccgc    1740
tttactgatt gtagcatcaa aagaaacttt tctttcctaa agtagatctc aaaggcaaaa    1800
agatgagttt ctatcttgtt cttcaccaag ttcttcaatg gtgttaaaaa cttaatagct    1860
tcttccaatg gagtttcaac cttggccagt ttctcaggga taagctcttc tttggggcct    1920
ccaatttctt cgtcatcatc atccttttc ttttcggat tccgttgcgg cttttctttt    1980
tcggcatttt ttttctcttc ttcaatctgg gctttctttt gagctcttct ttgtttatta    2040
cgcagtttct ttagctcttt gtcagacatg tttgctgtat cagcctcgtg ttctttgttc    2100
tcatctgtca gagggttgtc atgaagcttc aaatagatct caatagcaat tctcgctgct    2160
ttgaagtaaa atggatgctg tcgaagtaca tcttctagtt ttaataagtc cacatatgat    2220
ctaagggtga tcttcctcat acagtatgta tgaaagtcaa actggtcatc ggtgatttct    2280
ataaaatgtc tctcaatttc atgacatttc ttaagtgctt caccaaattt gttcattgct    2340
ttgtatgcct gagcacactc tgtctggaac cacatacact gcatttcatt caggttctct    2400
accgctgaag ttccttccct cgtaaacttg gaacacattt cttcagcctc tttaatcagg    2460
ttggctttta acatgtattt tgcacacttg gaattaataa atctgtctgc tgtgtccagg    2520
```

```
gcctgggctt catccatcca cctggcagct tctttaatat tcccagcatg cttatagatt    2580
ttagctttta caagaaagag ttctatcaat gttggtgtac tttcaattgc agtatttatg    2640
tattccagag caatggatgg ctgaccaatt ttatcataat gctgtgccaa atagtactgg    2700
acccaaagta atgtggttgg aggttcctcc tttccatcat cattggggtt aaataggcga    2760 caactttta gagaagtttc ataaccaact actagttctt ctacgattgc caccttctct    2820
ttatctctgt ataaagacct caaggtattg aagacaggtg gacagccctt gctgaaattc    2880
atccttagga acctatccaa acactcctta aacttctctc cagataaaaa gtttaagggc    2940
agctttcttg gcacgagtcc cctggggtat ttagtccagg cttcctcata tatttttagc    3000
cgttctaaca tattagctgg cttcagtgct ttttctaagc ctttgtaata ggcccaattt    3060
tcaggattcc tctcttgtaa tcctctataa acgtcagcag catcttccaa acgacacaac    3120
tgcaacagaa gttcccttt ggtttcttca acagcaagtt tatcacaaat ctgcttttca    3180
taggtacaaa gatgttccag ggcttctcta taaagacctg cttcccgaag aacttgattc    3240
tgatataaga ggagttcact atattcataa tccactttat caggagatgt ctgctgtgtt    3300
ttcctaaact cttctaaaat ttttgctgcc atttcatagt cttctaataa atggtaaagc    3360
ataaccaatc catgatgctc actctgcaga tcctctatca tcttgcgggt gttacttg     3418
```